United States Patent [19]

Whitehouse et al.

[11] 4,437,859
[45] Mar. 20, 1984

[54] HYDRAULIC SYRINGE DRIVE

[75] Inventors: Craig M. Whitehouse, New Haven; Nigel Cox, Cheshire; Allan G. Burt, East Haven; Daniel R. Snyder, New Haven, all of Conn.

[73] Assignee: DRS Infusion Systems, Inc., New Haven, Conn.

[21] Appl. No.: 287,861

[22] Filed: Aug. 3, 1981

[51] Int. Cl.³ .............................................. A61M 1/00
[52] U.S. Cl. ................................................ 604/131
[58] Field of Search ................ 604/131, 93, 141, 142, 604/143, 150, 149, 218, 236, 237, 152

[56] References Cited

U.S. PATENT DOCUMENTS

| | | | |
|---|---|---|---|
| 2,101,140 | 12/1937 | Hege | 604/143 |
| 3,605,745 | 9/1971 | Hodosh | 604/143 |
| 3,640,277 | 2/1972 | Adelberg | 604/141 |
| 3,690,318 | 9/1972 | Gorsuch | 604/141 |
| 4,065,230 | 12/1977 | Gezari | 604/150 |
| 4,150,672 | 4/1979 | Whitney et al. | 604/143 |

Primary Examiner—John D. Yasko
Attorney, Agent, or Firm—Peter L. Berger

[57] ABSTRACT

A syringe driving unit comprising free pistons in interconnected cylindrical chambers, one of the pistons carrying a syringe plunger driver and being biased, directly or indirectly, in the driving direction, and one piston being movable to force both pistons into primed or loaded position, the connections between the chambers including a pressure regulator, flow regulator and a needle valve to regulate adjustably the return flow or hydraulic fluid corresponding to the movement of the driving piston. The priming piston may be moved mechanically or pneumatically, and fail-safe mechanism may be provided, if needed, to become effective in case of leakage. Bolus delivery, to augment optionally the adjusted flow, is also provided for.

23 Claims, 21 Drawing Figures

HYDRAULIC SYRINGE DRIVE

This invention relates to a self-contained hydraulic drive device for continuously and automatically actuating a hypodermic syringe for administering fluid medicinal compositions to a patient's body.

BACKGROUND OF THE INVENTION

1. Field of the Invention

There are several, if not many, types of medical problems wherein the favored treatment calls for the administration of medicaments either at frequent intervals or at rates which are comparable to the protective and defensive reactions of certain body organs. Rapidly accumulating clinical evidence from humans and data from research using laboratory animals have led many diabetologists—that is, internists specializing in the diagnosis and treatment of diabetes—to believe that poor control of blood glucose levels is the prime factor in the development of later complications of diabetes. The goal of insulin therapy is to approximate pancreatic insulin secretion as closely as possible in order to avoid excessive swings in blood sugar levels. But with conventionally administered insulin, normal glucose levels (normoglycemia) are rarely attained, even in a hospital setting, and many severely insulin-deficient patients seldom or never have a negative urine glucose. The short-term consequences of poorly regulated intervals of hyper- and hypoglycemia are well known (irritability, lethargy, depressions, appetitive changes and so forth), but it is the long-term consequences which lead to the terrible consequences of chronic diabetes.

The preferred therapeutic approach is to deliver insulin in quantities as close to physiologic demand (the way the normal pancreas operates) as possible. Furthermore, clinical evidence indicates that maintenance of normal blood glucose levels might prevent the vascular complications or perhaps even reverse those already developing if caught early enough.

Slow, long-continued injections of medicaments for cancer chemotherapy, chronic pain therapy, hormonal deficiencies (other than from pancreatic failure) plasma infusion, and certain genetic diseases are also in need of means for the reliable automatic slow (but adjustable) delivery of medicaments.

2. Description of the Prior Art

The patented prior art presently known to applicant includes the following:

Kollsman U.S. Pat. No. 2,605,765, Aug. 5, 1952 for an Automatic Syringe which is portable and designed to effect subcutaneous injections at a predetermined rate.

Gidlund U.S. Pat. No. 3,349,767, Oct. 31, 1967 for an Injection Syringe adapted to introduce "great quantities" of liquid rapidly, as for x-ray contrast photography.

Hodosh et al., U.S. Pat. No. 3,768,472, Oct. 30, 1973 for a Fluid Dispensing Gun, a complicated mechanism adapted to shoot novocaine into a patient in aid of a surgical or dental procedure.

Kamen U.S. Pat. No. 3,858,581, Jan. 7, 1975, for a Medication Injection Device providing a motor-driven syringe for repetitive medication injection.

Bron et al., U.S. Pat. No. 4,007,739, Feb. 15, 1977 for a Fluid-Operated Hypodermic Syringe, particularly for medication of livestock.

Citrin U.S. Pat. No. 4,022,207, May 10, 1977, for an Actuator for a Syringe intended to dispense precise liquid quantities in an accurately repeatable manner, with single-hand control.

Wagner U.S. Pat. No. 4,114,619, Sept. 19, 1978 for Automatic Injecting Apparatus wherein the patient's skin is drawn into a tensed position against the needle tip before a hypodermic injection is performed.

Wuthrich et al., U.S. Pat. No. 4,059,110, Nov. 22, 1977 for a clockwork driven hypodermic syringe; the patent cites and discusses several prior patents on "mechanically-powered hypodermic syringes for medical or laboratory purposes" (including Kollsman, supra) and dismisses them as not pertinent to the invention which Wuthrich characterized as "relatively small and portable . . . comparatively simple to manufacture, and inexpensive."

Portner et al. U.S. Pat. No. 4,265,241 for an Implantable Infusion Device describes several embodiments each relying on externally transmitted signals to release doses of a medicament from a variable volume implanted container.

SUMMARY OF THE INVENTION

The syringe driving unit is hydraulic in nature and comprises two chambers with movable "pistons" or diaphragms. To prime the mechanism an incompressible fluid is forced from a first chamber into a second chamber, moving the piston in the second chamber back, and the piston in the first chamber forward. Fluid moving in this (priming) direction flows through a check valve connecting the two chambers. Fluid cannot flow from the second chamber into the first chamber through this check valve. When the unit has been primed, the force is released from the backside of the piston in the first chamber allowing the counteracting force applied on the backside of the piston in the second chamber to dominate. The direction of flow is then from the second chamber to the first chamber and the only available pathway for this flow is through a precision variable flow, regulating system. The regulation of the return flow allows accurate control of the rate of movement of both pistons. One of these pistons (depending on the exact nature of the flow regulating system) is connected to a bracket which moves the plunger of a syringe at a set rate, corresponding to the controlled movement of the piston. At any point in the piston (i.e., syringe plunger) movement, the rate may be changed or completely stopped. At any point, when desired, the drive unit may also be reprimed. Several variations can be effected in the details of the flow regulation, priming force, driving force, bolus delivery, piston construction, and side from which the syringe is driven, as will be set forth below.

OBJECTS OF THE INVENTION

An object of the invention is to provide a hydraulic drive for a syringe plunger wherein the fluid flow is controlled by a pressure regulator followed by an adjustable valve and/or adjustable flow regulator,
 whereby accurate flow rates are obtained over the entire plunger travel and a calibrated unit can remain accurate indefinitely.

Another object of the invention is to provide such a drive wherein changes in the flow rate can be effected without stopping the operation. This can be realized by adjustment of the continuously variable drive fluid flow rate, and use of discrete (or continuous) volume units of bolus delivery.

A further object of the invention is to provide such a drive which is adapted for use with many types and sizes of syringes.

A still further object of the invention is to provide such a drive which utilizes a hydraulic fluid whose viscosity remains virtually constant over the required operating temperature range.

Another object of the invention is to provide such a drive unit which is small, light in weight, compact, self-contained, durable, independent of environmental constraints, and adapted to be worn on or near the body.

A further object of the invention is to provide certain improvements in the form, construction and materials of the several parts whereby the above-named and other objects may effectively be attained.

The invention accordingly comprises the features of construction, combination of elements and arrangement of parts, which will be exemplified in the construction hereinafter set forth, and the scope of the invention will be indicated in the claims.

Referring to the drawings, and particularly FIGS. 1 to 11, the syringe drive elements are shown as being built in, or enclosed in, a fabricated plastic case or housing 11, preferably of a high impact material such as polycarbonate, which is provided with a first cylindrical chamber 12 (the priming chamber), a second cylindrical chamber 13 (the driving chamber) and a syringe chamber 14, the last being closed by a slidable lid 15.

Figures 2, 5, 7:
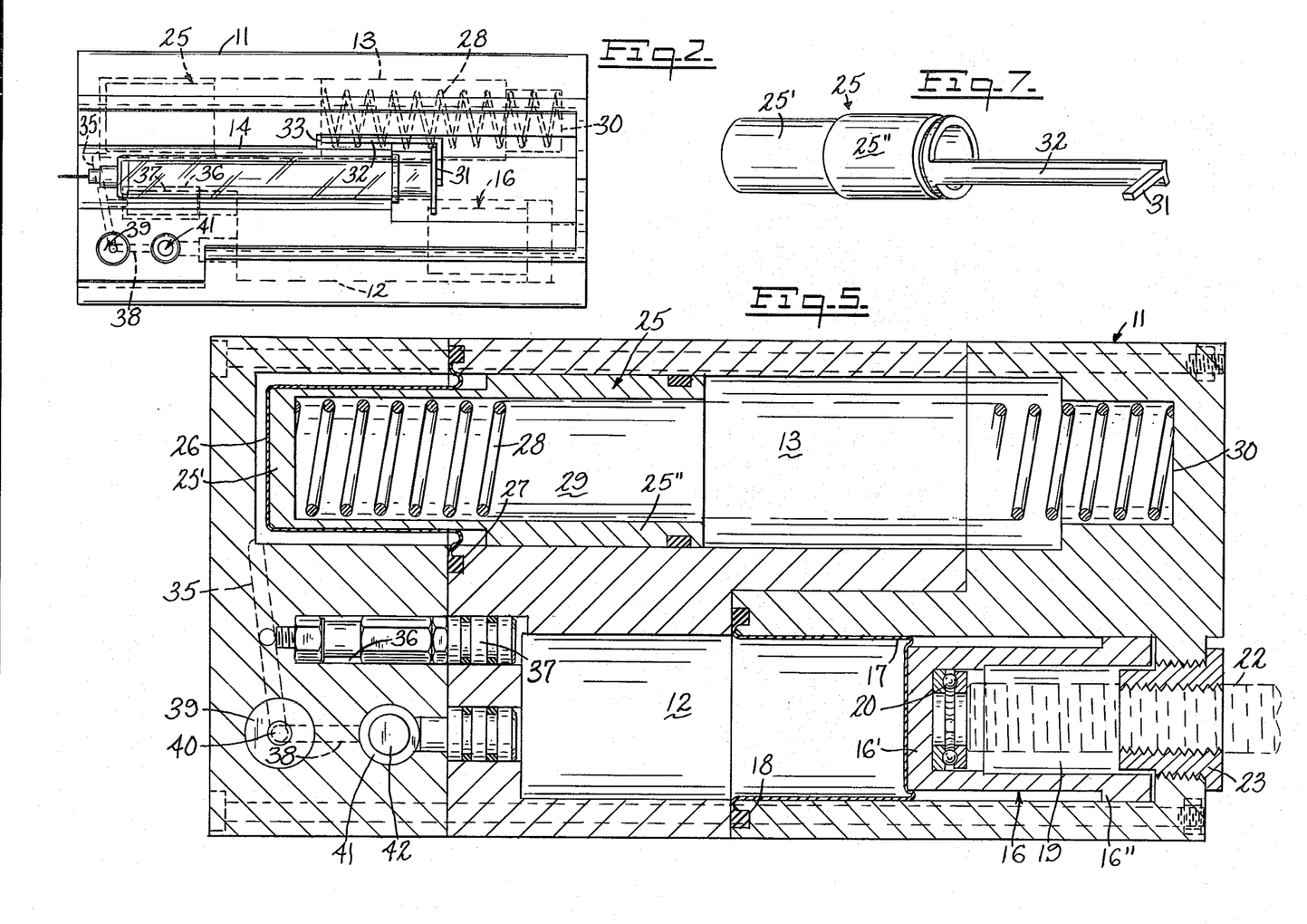
FIG. 2 represents a top plan view of this version of the syringe drive, with lid removed.
FIG. 5 represents a horizontal section on the line V—V of FIG. 1 on a larger scale, and showing the parts in unloaded position.
FIG. 7 represents a detail perspective view of the plunger-driving piston.
Figure 3:
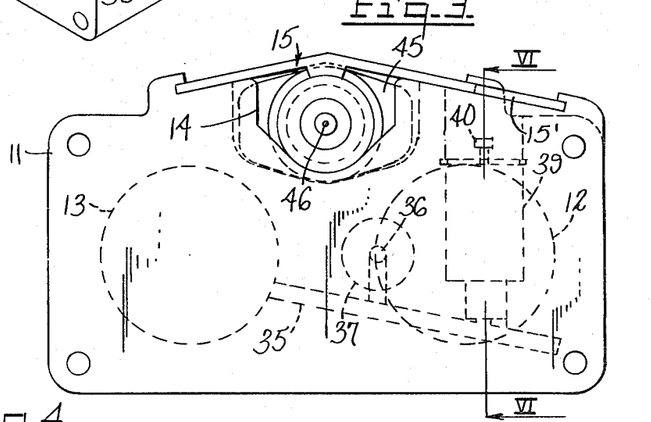
FIG. 3 represents a needle-end elevation of the syringe drive shown in FIGS. 1 and 2.
Figure 4:
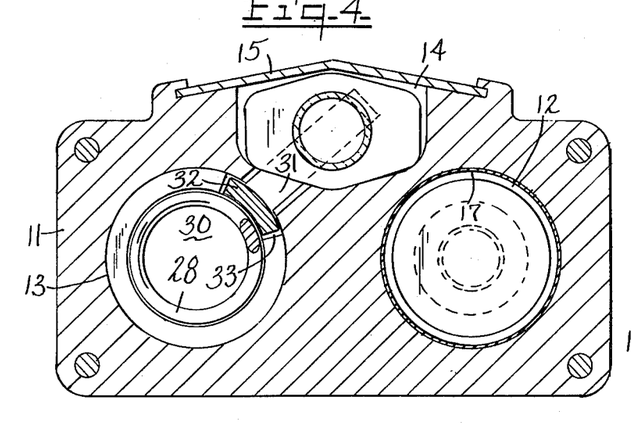
FIG. 4 represents a transverse vertical section on the line IV—IV of FIG. 1.
Figure 6:
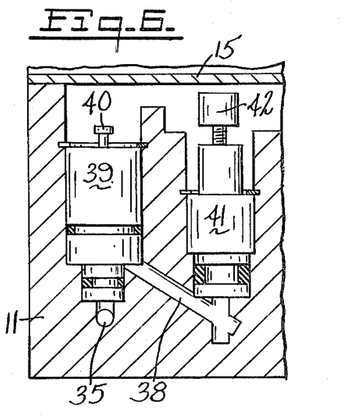
FIG. 6 represents a detail vertical section on the line VI—VI of FIG. 3.

The priming chamber 12 is shown in FIG. 5 as being fitted with a piston 16 having a reduced diameter forward end 16' which bears against the central portion of a cup-shaped rolling diaphragm 17. The free edge of the diaphragm is firmly sealed in the annular slot 18 intermediate the ends of the chamber. The rear end portion of the piston 16 has an enlarged diameter annular flange 16" which has a free sliding fit in the chamber. A deep axial recess 19 extends into the piston from its rear end and a bearing assembly 20 is set in the forward end of the recess.

A drive for the piston 16 is provided in the form of a screw 22 threaded in a plug 23 which, in turn, is screwed into an aperture in the adjacent end of the case, the front end of the screw being adapted to bear against one race of the bearing assembly 20. The screw is preferably provided with a knurled knob (not shown) for convenient manipulation.

The second chamber 13 is shown as being provided in the case 11 in a position parallel to the first chamber and provided with a piston 25 having a reduced diameter portion 25' and a larger diameter portion 25". A cup-shaped rolling diaphragm 26 has its free edge sealed in the annular slot 27 while its central portion bears against the forward end of the piston 25. The piston is strongly biased toward the forward end of the chamber by a helical spring 28, fitted in the recess 29 in the piston and bearing against the opposite end wall 30 of the chamber. The piston 25 has a syringe plunger driving arm 31 projecting radially from the extension 32 which is preferably integral with the piston and extends rearward from the portion 25". The wall of the chamber is cut away as shown at 33 (FIG. 4) to permit passage and movement of the driving arm.

Figure 1:
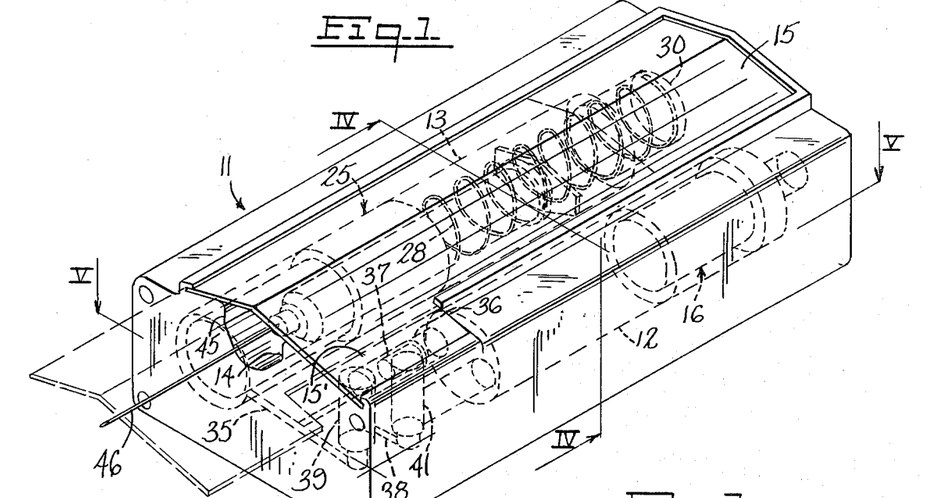
FIG. 1 represents a perspective view of a first form of the syringe drive, a partially open position of the lid or cover being indicated in broken lines.

The forward end of the chamber 13 is in communication with a conduit 35, which communicates with the forward end of chamber 12 through conduit 36 containing check valve 37, and a parallel conduit 38 whose flow from chamber 13 is restricted by a pressure regulator 39, adjustable by means of knob 40 (mainly for calibration purposes), and needle valve 41, adjustable by means of knob 42. The recesses in which regulator 39 and valve 41 are mounted can be fabricated in the parts of the case or housing 11 and provided with fluid-tight seals as needed, in a conventional manner. The regulator 39 and valve 41 are mounted vertically, so that their adjusting knobs 40 and 42 are readily accessible (FIG. 6) beneath the lateral extension 15' of the slidable lid (FIG. 1).

The syringe chamber 14 is of a size and shape to accommodate syringes in a range of sizes and the front wall of the case is cut away at the top, as shown at 45, to permit free projection of the syringe needle 46 or other tubular connection for delivery of the contents of the syringe. In every case, means must be provided to prevent forward movement of the syringe barrel, either by contact with the wall of the case or by other means.

The apparatus shown in FIGS. 1 through 7 is designed to be operated as follows:

In loaded, but not primed, condition the pistons should be in the positions shown in FIG. 5. The forward end of chamber 13 and all space between the diaphragm 17 and the diaphragm 26 in chamber 12 is filled with a suitable fluid, incompressible, non-volatile, temperature-stable and a fluid which maintains relatively constant viscosity over a specified temperature range. (e.g. silicon oil). The unit may be kept indefinitely in this passive state. To prime the unit, for syringe driving, the screw 22 is actuated to force the piston 16 into the chamber 12, thereby causing the liquid to flow (mainly through the one-way check valve 37) through conduit 35 into chamber 13 where it pushes back the piston 25 against the force of spring 28. This spring is shown as a coil spring however with suitable modifications to the shape of the case, constant force springs may be alternatively employed. In its fully primed position the driving arm 31 on piston 25 should permit the introduction of a fully loaded syringe into the chamber 14, with the plunger driving arm near or against the driving arm. The assembly is then ready to be applied to a patient and activated by backing off the screw 22 from the piston 16, which is thereafter subjected only to hydraulic force of the liquid passing through conduit 35, pressure regulator 39 and needle valve 41. The length and strength of the spring 28 must be adequate to ensure high enough impact pressure into the pressure regulator to maintain proper regulation of the flow. After the pressure regulator has been set, the absolute rate of flow is regulated by adjustment of the needle valve 41, which can be adjusted at any time without interrupting the administration of medicaments from the syringe.

A modified form of apparatus is shown in FIGS. 8 to 11. The case or housing 51 is similar to the case 11 and the chambers 52, 53 and 54 correspond to chambers 12, 13 and 14, with similar interconnections. The diaphragms 17 and 26 are eliminated and the pistons 55, 56 are made fluid-tight in their respective chambers by means of sealing rings or O-rings indicated generally at 57 and 58. An unobstructed hydraulic or pneumatic fitting 59 is substituted for the screw 22, in order to allow pressurized priming of the piston 55. This pressurized priming may be used with all described versions of this device. A syringe plunger driver 60 is mounted on the piston 56 by means of the piston extension 61 (like 32) with which is associated a fail-safe mechanism.

Figure 9:
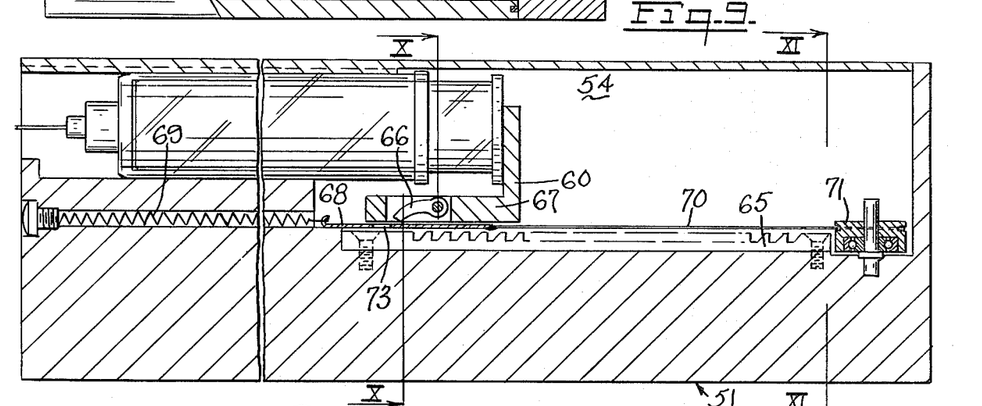
FIG. 9 represents a vertical longitudinal section showing a safety brake which is an optional feature in any form of the syringe drive.
Figure 10:
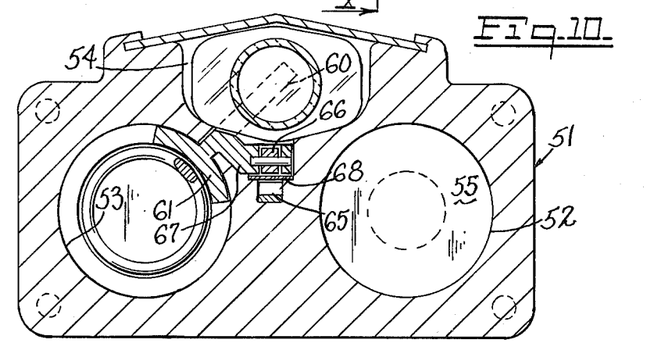
FIG. 10 represents a transverse section on the line X—X of FIG. 9.
Figure 11:
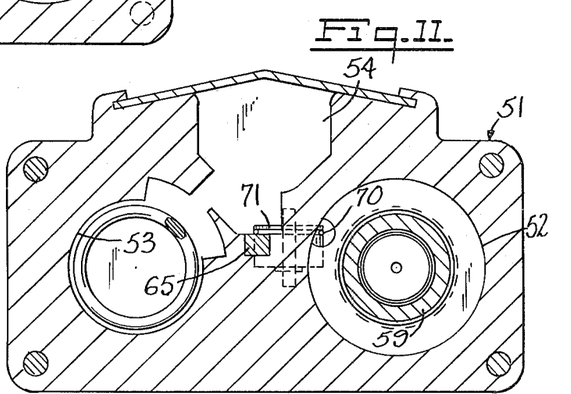
FIG. 11 represents an end elevation of the syringe drive shown in FIGS. 9 and 10.

Such a mechanism is shown in FIGS. 9, 10 and 11 as comprising a rack 65 mounted in the case and extending beneath and parallel to the path of travel of the driver 60 (FIG. 9). A pawl or latch 66 is pivotally mounted in a branch 67 of the extension 61 which projects over the rack, the pawl being biased, as by a spring (not shown), toward a position of engagement with the teeth of the rack. During normal operation of the syringe drive, the pawl is prevented from engaging the rack by the flat shielding strip 68 which lies over the teeth of the rack and is biased toward the front end of the case by a light spring 69 attached to one end of the strip. The other end of the strip is attached to a wire or other filament 70 which passes around a drum or pulley 71 and has its free end attached to the rear of the piston 55. Since the pistons 55 and 56 are hydraulically interconnected, the movement of piston 55 in either direction will be accompanied by simultaneous movement in the opposite direction of piston 56 and strip 68. During such simultaneous movements, the pawl 66 rests on the strip and is prevented from engaging the teeth of the rack. The strip is, however, provided with an aperture 73 adjacent to the pawl's point of contact with the strip (FIG. 9); if accidental leakage of fluid from the chamber 53, in front of piston 56, should occur, the piston will only move a short distance before the pawl drops through the aperture 73 into engagement with the rack and the emptying of the syringe is immediately arrested. If this fail-safe mechanism is included in the diaphragm form of the apparatus (FIGS. 1 to 7), it could be activated by the accidental rupture of the diaphragm 26, in front of piston 25, or because of fluid leakage due to any other cause, permitting an uncontrolled advance of the syringe plunger driver (31 or 60).

Figure 8:
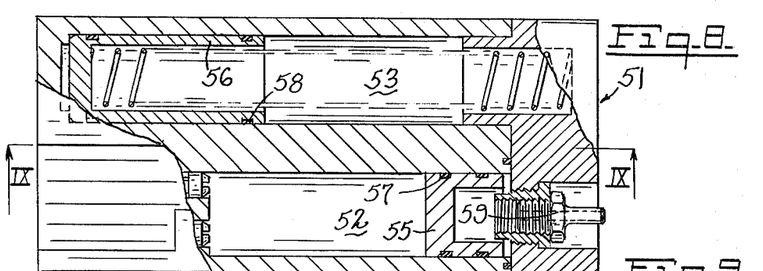
FIG. 8 represents a horizontal section, similar to FIG. 5 but on a smaller scale, of a second form of the syringe drive.

In a third and presently preferred alternative embodiment of the invention, shown in FIGS. 14 to 21, the case or housing 90 is fabricated to provide first and second cylindrical chambers 91, 92, fitted with pistons 93, 94, respectively, which are similar to the pistons 12 and 13 in FIG. 5, each piston having a reduced diameter end 93', 94' adapted to cooperate with a respective flexible diaphragm 95, 96. The diaphragm arrangement, when used, is similar to the structure shown in FIG. 5 and described in connection with that figure, so that the details will not be repeated. Alternatively, the pistons could be sealed as shown in FIGS. 8 and 9, without the use of diaphragms.

The third embodiment is characterized particularly by the addition of a flow regulator downstream from the pressure regulator and needle valve in the flow regulating pathway from chamber 92 to 91. This increases the accuracy of the flow regulation and allows the syringe plunger driver to be attached to piston 93, (the opposite piston to that of configuration 1 FIG. 5). This eliminates the need for the additional failsafe as was illustrated in FIG. 10. With the syringe driven from piston 93 of FIG. 14, a failure involving loss of the regulating hydraulic fluid will immediately stop any forward movement of the syringe plunger driver (i.e. the unit will fail in the off mode). Since the pistons move in opposite directions, the change in function of the priming piston requires reversal of the syringe chamber 97 (FIG. 15) wherein the syringe S with plunger P is mounted with its needle or nozzle end N exiting the case or housing at the end where the priming force is applied to the first piston 93. This piston is provided with a deep axial recess 99 extending into the piston from its rear end and a bearing assembly 100 is set in the forward end of the recess which also contains a helical spring 101 under compression.

Figure 14:
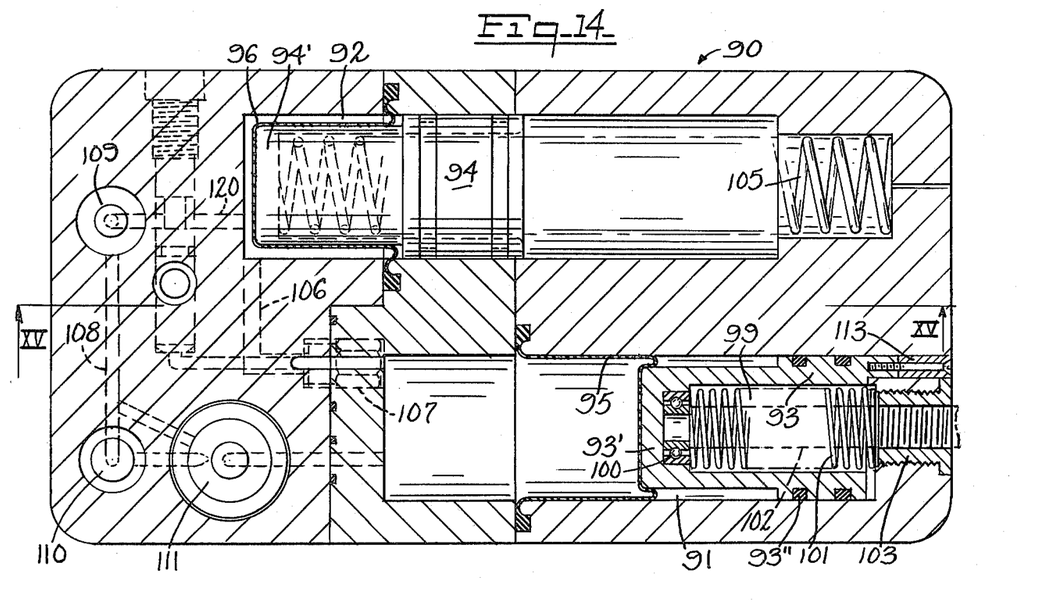
FIG. 14 represents a longitudinal horizontal section through a third form of syringe drive.

The priming force for the piston 93 is provided by a screw 102 threaded in a plug 103 which, in turn, is screwed into an aperture in the end of the case, the front end of the screw (which passes freely through the spring 101) being adapted to bear against one race of the bearing assembly 100. The screw is preferably provided with a knurled knob (not shown) for convenient manipulation.

The second chamber 92 is fabricated into the case 90 in a position parallel to chamber 91 and contains the piston 94 cooperating with its diaphragm 96. The piston is cup-shaped and is strongly biased forward by a spring or spring assembly 105, as in the case of piston 25 (FIG. 5).

It is noted here for completeness that in certain restricted applications the main spring 105 and piston 94 may be removed entirely and the driving force may be a compressible fluid introduced under pressure into a sealed chamber (analogous to 92) behind the diaphragm.

The forward end of chamber 91 communicates with the forward end of chamber 92 by means of the conduit 106 in which is interposed the check valve 107, permitting flow only from 91 to 92. The return flow, from chamber 92 to chamber 91 takes place only by way of the conduit designated generally as 108 which connects chamber 92, first, to the pressure regulator 109, then to the needle valve 110 and through the flow regulator 111 to the chamber 91. The conduits 106 and 108 together with interconnected portions of the chambers 91, 92 and control elements 109, 110 and 111 are filled with a constant volume of incompressible fluid, exemplified by a silicon oil.

Figure 15:
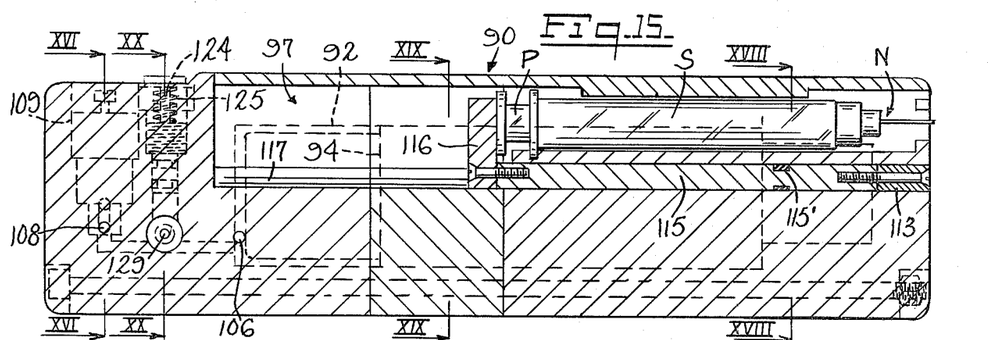
FIG. 15 represents a vertical section on the line XV—XV of FIG. 14.

In order that the syringe plunger may be driven by the piston 93 the latter has mounted on its rear end a connecting bracket 113, which projects radially through an axially disposed slot 114 in the wall of the chamber 91 and carries at its free end a rod 115 passing through a bore which lies parallel to the axis of the chamber 91. At its other end the rod 115 is provided with a plunger bracket 116 projecting into the syringe chamber in a position to bear against the plunger of a syringe when the latter is introduced into the chamber 97, as shown in FIG. 15. The bottom wall of the chamber 97 is longitudinally slotted at 117 to permit free guided movement of the plunger bracket in its syringe actuating mode.

In operation, the third embodiment described above is primed or charged by screwing inward the threaded rod 102 (like rod 22) or by utilizing hydraulic or pneumatic means as in FIG. 8 whereby the piston 93 is moved forward forcing fluid in chamber 91 to pass through the check valve 107 and conduit 106 into the chamber 92. This moves the piston 94 rearward against the force of the spring 105, while the advancing piston 93 carries with it the rod 115 and the plunger bracket 116 which, when the priming is completed, is ready to engage the plunger of a loaded syringe (as in FIG. 15) which is then put in place. Upon removal of the priming force (threaded rod 102 or other means), the force of spring 105 tends to advance the piston 94 and thus drive the fluid from chamber 92 through the conduit 108 and its associated control elements, this flow being inhibited initially by manually closing the needle valve 110. When correct adjustment of the pressure regulator 109 is set and flow regulator 111 has been adjusted to the flow range needed, the needle valve is opened to the desired setting and the medicament in the syringe will be delivered as required.

Spring 101 is a much weaker spring than the driver springs 105. Since piston 93 has no tight seals between chamber 91 and the backside of the diaphragm, it is free to float. Because the unit is to be worn on the body, it is expected to go through fairly rough treatment. During operation if piston 93 were to free float, the syringe plunger would be the only impedance to its backward movement. From the weight of piston 93 alone, this could result in some unwanted pulses on the syringe plunger. To prevent this occuring spring 101 is used to hold piston 93 firmly against diaphragm 95 and friction rings 115' and 93" are placed around rod 115 and piston 93 respectively, to damp out any sudden movement of piston 93. (A sudden movement could come from a shock or hit to the case for example).

The pressure regulator 109 has an adjustment knob which is primarily to set the output pressure during calibration, and is generally not moved after that by the user; the pressure regulator maintains a constant pressure at its output channel 108 over the entire specified flow range.

Figure 17:
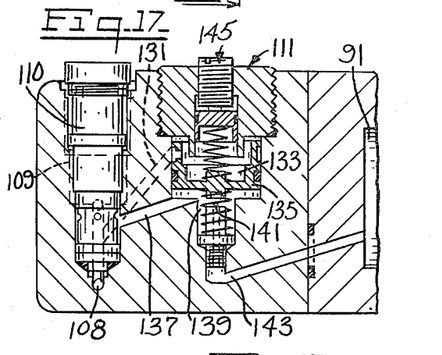
FIG. 17 represents a vertical section on the line XVII—XVII of FIG. 16.
Figure 18:
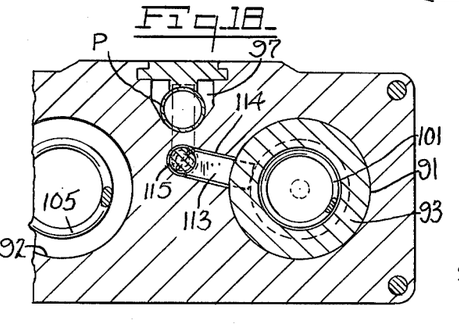
FIGS. 18, 19 and 20 represent vertical sections on the lines XVIII—XVIII, XIX—XIV, and XX—XX, respectively of FIG. 15.
Figure 19:
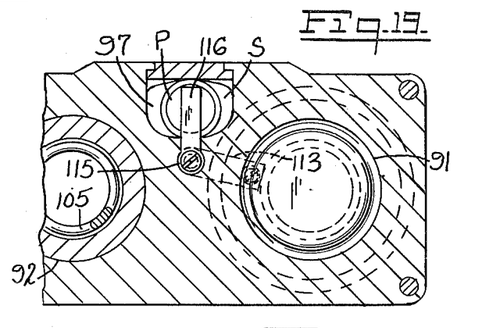
Figure 21:
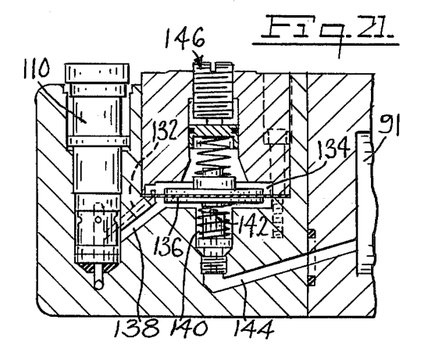
FIG. 21 represents a detail vertical section showing a modified form of flow regulator.

The details of construction of alternative forms of flow regulators are shown in FIGS. 17, (piston) and 21, (diaphragm), wherein channel 131 or 132 conducts constant pressure fluid from the conduit 108 entering the needle valve 110 to the chamber 133 or 134, above the piston 135 or diaphragm 136, while channel 137 or 138 connects the output of the needle valve with the chamber 139 or 140 beneath the piston 135 or diaphragm 136.

By adjustment of 145 (or 146) a set pressure drop across the needle valve 110 due to flow through it will be maintained by the moving piston or diaphragm interacting with orifice 141 (or 142). Flow from the chamber 139 or 140 proceeds through the small orifice 141 or 142 to the conduit 143 or 144 and thence into the chamber 91. The rate of flow through the orifice 141 or 142 is controlled by the position of the piston 135 or diaphragm 136 which is a function of the fluid pressure difference on opposite sides of the piston or diaphragm and the adjustable spring assembly 145 or 146. This adjustment, once made, generally need not be altered by the user.

Flow rates through the regulating pathway may be kept constant for the entire run (i.e. until piston 94 has moved back to the end of its stroke); or may be changed at any point during the run. At any point during a run the flow may be stopped altogether by closing needle valve 110. The unit may also be reprimed at any time. Adjustment of the needle valve alone may not give the full range of flow desired. Simultaneous adjustment of the needle valve and the flow regulator 111 will allow regulation of flow over a larger range.

While it is a primary objection of the invention to provide means for supplying medicaments at a slow uniform rate, it must be recognized that circumstances might render it advisable or essential to administer at some point in time, an augmented quantity of medicament without disrupting more than momentarily the established steady supply. For instance, during the course of emptying a syringe of insulin over a 24 hour period, an increased rate of injection may be desired, say, before a meal. A bolus delivery means may be included in the drive unit versions as shown in FIGS. 12, 13, 14 and 20. This feature serves several useful purposes. It allows an increase in the movement rate of the plunger bracket 31 or 116 without having to change the set regulated flow rate. For instance, when a person loads a syringe into the unit, he may move the plunger bracket up to meet the plunger by using the bolus pin.

Figures 12, 13:
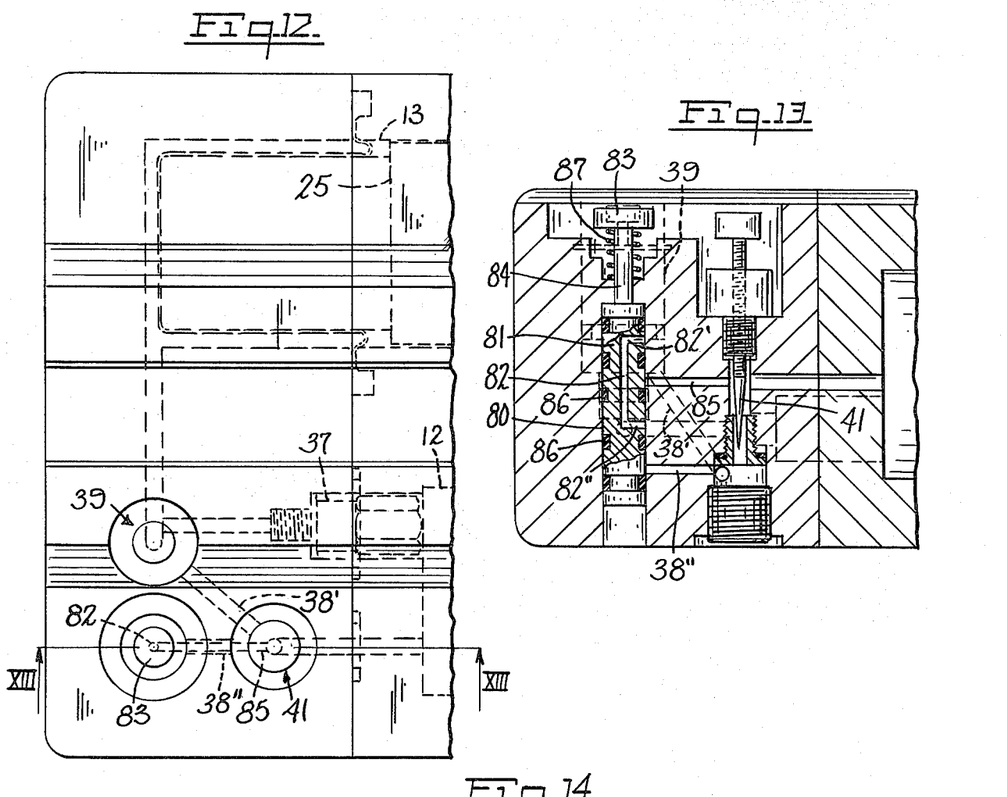
FIG. 12 represents a detail plan view of an end zone of the syringe drive housing of the first form showing the location of the needle, as in FIG. 6, with a "bolus injector" added.
FIG. 13 represents a cross-sectional view on the line XIII—XIII of FIG. 12.
Figure 16:
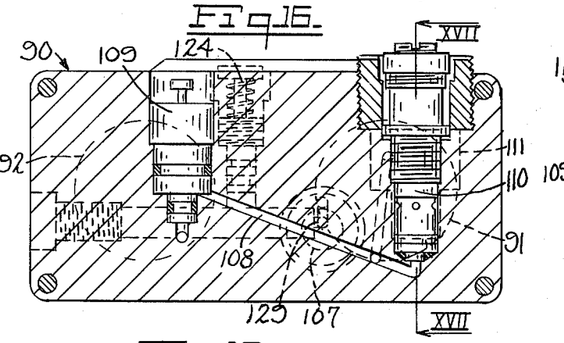
FIG. 16 represents a vertical section on the lines XVI—XVI, of FIG. 15.
Figure 20:
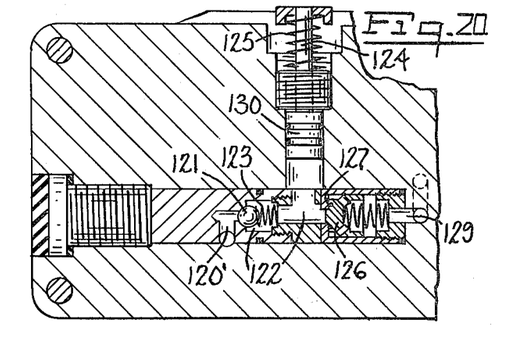

Two possible versions of a bolus delivery are illustrated, one in FIGS. 12 and 13, the second in FIGS. 14, 16, and 20. The first causes continuous increased plunger movement as long as the bolus pin is held down. With the second version, each press of the bolus pin advances the syringe plunger a discrete preset amount regardless of how long the bolus pin is held down. First the continuous delivery bolus will be described in connection with the first form of the drive unit shown in FIG. 5. In FIGS. 12 and 13 there is shown a bypass slide valve which may be interposed between the needle valve and pressure regulator and operated manually to admit into the conduit 38" (connected to 38') a quantity of the control fluid, bypassing the restrictive orifice of the needle valve but retaining the control of the pressure regulator.

To this end the instrument case is provided with a cylindrical valve chamber 80, parallel and adjacent to the chambers housing the needle valve 41 and pressure regulator 39. A slider valve post 81 traversed by a passage 82 is slidable in the chamber 80 under the control of a button 83 connected to the valve slider by the stem 84. The passage 82 has an upper end 82' in radial alignment with a bleed passage 85 from the needle valve 41' and a lower end 82" which may be brought into communication with the conduit 38'. The valve is shown as having several annular seal rings 86 to ensure fluid tightness and a spring 87, beneath the button 83, holds the valve normally closed. The passage 82 is so proportioned and oriented that it may, by depression of the button 82, be brought into a position such that its upper end 82' registers with passage 85 when its lower end 82" registers with conduit 38". At that point the restrictive orifice of the needle valve is bypassed and the fluid flow rate can increase according to the size of 82 to expedite movement of the syringe plunger driver, whereby an additional slug or "bolus" of the medicament can be delivered to the patient.

An alternative discrete bolus delivery mechanism is shown in FIGS. 15, 16 and 20, this being particularly useful in the insulin oriented drive unit. It comprises a small manually driven piston pump, which may be actuated at any time after the overall drive unit has been primed. Referring to FIG. 20, fluid from chamber 92 passes via channel 120' through a check valve 121 on the input side of the bolus delivery. The valve consists of a ball which moves inside chamber 122 and is held against its seat by a fairly weak spring 123. Due to the direction of this check valve when pin 124 is up, it is held there by spring force from 125, and the pressure in chamber 122, (which is the same as that of chamber 92). Channel 129 connects chamber 122 to chamber 91. During operation of the drive unit, the pressure in chamber 122 is always higher than in chamber 91. The spring 125 is chosen strong enough to hold plug 126 tightly enough against the valve seat 127 for the 0-ring on the plug to seal completely. Thus with pin 124 in the up position, no flow at all goes through the bolus feed in its quiescent state. When the bolus pin 124 is pushed down, the pressure in chamber 122 increases forcing ball 121 against its seat and overcoming the counteracting spring force exerted against plug 126. As the bolus pin moves down, the piston 130 displaces fluid from chamber 122 forcing it into chamber 91. One full stroke of the bolus pin forces only a set volume of fluid from chamber 122 into chamber 91 corresponding to the volume displaced by piston 130. When the piston 130 reaches the bottom of its stroke plug 126 is again forced against its seat by the spring force behind it. The pin may be held down indefinitely with no further fluid flow occuring through the bolus delivery. When the bolus pin is released, fluid enters from chamber 92 flowing by ball 121 into chamber 122, the bolus pin rises due to the force of spring 125 and the pressure in chamber 92 relative to ambient. The bolus pin may be actuated at any time during normal functioning (or even priming) of the drive unit, without affecting the regulated flow pathway.

It is noted with all the drive unit configurations illustrated (FIGS. 5, 8, and 14) that flow regulation is independent of changes in ambient pressure. The pressure regulator references to ambient as does the main driving spring chamber (i.e. 13 in FIG. 5 and 92 in FIG. 14) and the priming chamber (12 in FIG. 5 and 91 in FIG. 14). The drive unit flow and its regulation is maintained from the spring force alone and is completely insensitive to fluctuations in the ambient pressure or medium. The unit may be worn while swimming, that is, immersed in a liquid, as well as in air. The unit is constructed of highly durable material so adverse environmental conditions such as rain or salt water will not impair its performance.

The case or housing 11 can conveniently be fabricated in a plurality or parts adapted for assembly into the complete form shown, or one or more of the interior elements (chambers, etc.) can be made separately and assembled in a more or less box-like container, at the option of the manufacturer. The object of providing a lightweight, impact resistant readily portable, unit having the capabilities described should generally be kept in mind.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

What I claim is:

1. An automatic drive for a hypodermic syringe having a barrel for containing a fluid medicament and a plunger adapted to eject said medicament, the drive comprising a housing, means in said housing for supporting a syringe in operative position, first and second variable volume chambers each having a movable wall element, a conduit interconnecting said chambers to constitute a constant voluem capacity, a substantially incompressible fluid filling said capacity, means associated with the first chamber for forcing fluid contained therein into the second chamber, a syringe driver associated with one of the movable wall elements and operatively engageable with the syringe plunger, means biasing the movable wall element of the second chamber in a fluid-expelling direction, adjustable means associated with the conduit for accurate metering of the fluid flow from the second chamber to the first chamber, said adjustable means automatically operative to adjust the fluid flow during the operation of said automatic drive to maintain said fluid flow constant responsive to ambient pressure and to pressure changes upstream and downstream of said adjustable means.

2. An automatic syringe drive according to claim 1 which includes a one-way check valve between the first and second chambers.

3. An automatic syringe drive according to claim 1 or 2 wherein the flow metering means includes an adjustable needle valve.

4. An automatic syringe drive according to claim 3 wherein the flow metering means includes an adjustable constant pressure regulator.

5. An automatic syringe drive according to claim 1 or 2 wherein the flow metering means includes an adjustable flow regulator.

6. An automatic syringe drive according to claim 3 which includes manually actuated means for controllably bypassing at least a portion of the flow metering means.

7. An automatic syringe drive according to claim 1 which includes a fail-safe device adapted to arrest the movement of the syringe driver upon the occurrence of leakage of fluid from the constant volume capacity.

8. An automatic syringe drive according to claim 7 wherein the fail-safe device comprises a rack fixed to the housing, a latch element movable with the syringe driver along a path adjacent the rack and shielding means operable to prevent engagement of the latch element with the rack during normal operation and permit such engagement upon the occurrence of a movement of the second chamber wall element without movement of the first chamber wall element.

9. An automatic syringe drive according to claim 1 wherein the syringe driver is associated with the movable wall element of the second chamber.

10. An automatic drive for a hypodermic syringe having a barrel for containing a fluid medicament and a plunger adapted to eject said medicament, the drive comprising a housing, means in said housing for supporting a syringe in operative position, first and second cylindrical chambers, each chamber being provided with a movable piston defining a variable volume, a conduit interconnecting said variable volumes to constitute a constant volume capacity, a constant volume of a substantially incompressible fluid filling said capacity, means associated with the first chamber piston for moving said piston to force fluid through the conduit into the second chamber, a syringe drive associated with one of the pistons and operatively engageable with the syringe plunger, means biasing said second chamber piston in a fluid-expelling direction, means associated with the conduit for metering the flow of fluid from the second chamber to the first chamber, said flow metering means automatically operative to adjust the fluid flow during the operation of said automatic drive to control said fluid flow responsive to ambient pressure changes and to pressure changes upstream and downstream of said flow metering means.

11. An automatic syringe drive according to claim 10 which includes a one-way check valve between the first and second chambers.

12. An automatic syringe drive according to claim 10 wherein the flow metering means includes an adjustable needle valve.

13. An automatic syringe drive according to claim 12 wherein the flow metering means includes an adjustable constant pressure regulator.

14. An automatic syringe drive according to claim 12 or 13 wherein the flow metering means includes an adjustable flow regulator.

15. An automatic syringe drive according to claim 12 which includes manually actuated means for optionally bypassing at least a portion of the flow metering means.

16. An automatic syringe drive according to claim 10 wherein the syringe drive is associated with the piston in the first chamber.

17. An automatic syringe drive according to claim 10 wherein the means for moving the first chamber piston to force fluid into the second chamber is a screw.

18. An automatic syringe drive according to claim 10 wherein the means for moving the first chamber piston to force fluid into the second chamber is pneumatic.

19. An automatic syringe drive according to claim 10 wherein cup-shaped diaphragms are associated with each piston.

20. An automatic syringe drive according to claim 10 wherein each piston has a fluid-tight fit in its respective cylinder.

21. An automatic syringe drive according to claim 1 or 10 wherein the second chamber biasing means is at least one spring.

22. An automatic syringe drive according to claim 1 or 10 wherein the second chamber biasing means is compressed air.

23. An automatic syringe drive according to claim 4 or 13 wherein the regulating pathway is adapted to function independently of ambient pressure and ambient medium.

* * * * *